United States Patent
Singh et al.

(10) Patent No.: US 10,566,659 B1
(45) Date of Patent: Feb. 18, 2020

(54) EUTECTIC MIXTURES CONTAINING ALKALI-METAL SULFONIMIDE SALTS, AND ELECTROCHEMICAL DEVICES UTILIZING SAME

(71) Applicant: SES Holdings Pte. Ltd., Singapore (SG)

(72) Inventors: Rajendra P. Singh, Woburn, MA (US); Shubha Nageswaran, Billerica, MA (US); Qichao Hu, Arlington, MA (US)

(73) Assignee: SES Holdings Pte. Ltd., Singapore (SG)

( * ) Notice: Subject to any disclaimer, the term of this patent is extended or adjusted under 35 U.S.C. 154(b) by 0 days.

(21) Appl. No.: 16/530,805

(22) Filed: Aug. 2, 2019

Related U.S. Application Data

(60) Provisional application No. 62/779,772, filed on Dec. 14, 2018.

(51) Int. Cl.
| | |
|---|---|
| *H01M 10/0567* | (2010.01) |
| *H01M 10/0568* | (2010.01) |
| *H01G 11/64* | (2013.01) |
| *C01D 13/00* | (2006.01) |
| *C01D 15/00* | (2006.01) |
| *C01D 17/00* | (2006.01) |

(52) U.S. Cl.
CPC ........ *H01M 10/0567* (2013.01); *C01D 13/00* (2013.01); *C01D 15/00* (2013.01); *C01D 17/003* (2013.01); *H01G 11/64* (2013.01); *H01M 10/0568* (2013.01); *H01M 2300/0045* (2013.01)

(58) Field of Classification Search
CPC ......... H01M 10/0567; H01M 10/0568; H01M 2300/0045; H01G 11/64; C01D 13/00; C01D 15/00; C01D 17/003
See application file for complete search history.

(56) References Cited

U.S. PATENT DOCUMENTS

| | | | |
|---|---|---|---|
| 8,257,868 B2 | 9/2012 | Hagiwara et al. | |
| 8,377,406 B1* | 2/2013 | Singh | C01G 29/00 423/365 |
| 2007/0042266 A1 | 2/2007 | Oh et al. | |
| 2007/0099080 A1 | 5/2007 | Pickett, Jr. et al. | |
| 2009/0068565 A1* | 3/2009 | Lee | H01M 10/0567 429/331 |
| 2011/0111308 A1 | 5/2011 | Halalay et al. | |
| 2011/0143212 A1 | 6/2011 | Angell et al. | |
| 2012/0058393 A1* | 3/2012 | Fukunaga | H01M 4/381 429/200 |
| 2012/0088139 A1* | 4/2012 | Sakai | H01M 4/661 429/103 |
| 2016/0190643 A1 | 6/2016 | Kim et al. | |
| 2016/0261000 A1* | 9/2016 | Zhang | H01M 4/40 |
| 2018/0273866 A1 | 9/2018 | Joshi et al. | |

OTHER PUBLICATIONS

Zhang, H., Feng, W., Nie, J., Zhou, Z.—Recent progress on electrolytes of fluorosulfonimide anions for improving the performances of rechargeable Li and Li-ion battery, Journal of Fluorine Chemistry 174 (2015), pp. 49-61 (Year: 2015).*

Kubota, Keigo et al.; Thermal Properties of Alkali Bis(fluorosulfonyl)amides and Their Binary Mixtures; J. Chem. Eng. Data 2010, 55, 3142-3146; May 25, 2010.

Kubota, Keigo et al.; Novel inorganic ionic liquids possessing low melting temperatures and wide electrochemical windows: Binary mixtures of alkali bis(fluorosulfonyl)amides; Electrochemistry Communications 10 (2008) 1886-1888.

Shu, Zhang et al.; Instability of lithium bis(fluorosulfonyl)imide (LiFSI)-potassium bis(fluorosulfonyl)imide (KFSI) system with LiCoO2 at high voltage; Chin. Phys. B., vol. 24, No. 7 (2015) 078201.

Liu, Yali et al.; Molten salt electrolyte based on alkali bis(fluorosulfonyl)imides for lithium batteries; Electrochimica Acta; 105 (2013) 524-529.

Xu, Fei et al.; Molten salt of lithium bis(fluorosulfonyl)imide (LiFSI)-potassium bis(fluorosulfonyl)imide (KFSI) as electrolyte for the natural graphite/LiFePO4 lithium-ion cell; Electrochimica Acta 135 (2014) 217-223.

* cited by examiner

*Primary Examiner* — Anca Eoff

(74) *Attorney, Agent, or Firm* — Downs Rachlin Martin PLLC

(57) ABSTRACT

Binary and ternary eutectic mixtures and corresponding electrolytes are disclosed. In some embodiments, binary eutectic mixtures and electrolytes each include a first salt, $X1^+Y1^-$, and a second salt, $X2^+Y2^-$, wherein each of $X1^+$ and $X2^+$ is an alkali metal cation and $X1^+$ is different from $X2^+$; and each of $Y1^-$ and $Y2^-$ is a sulfonimide anion and $Y1^-$ is different from $Y2^-$. In ternary eutectic mixtures and electrolytes further include a third salt, $X3^+Y3^-$, wherein $X3^+$ is different from each of $X1^+$ and $X2^+$. In some embodiments, the eutectic mixtures and electrolytes have melting points in a range of about 5° C. to about 70° C. Electrochemical devices containing such eutectic-mixture electrolytes are also disclosed.

30 Claims, 1 Drawing Sheet

EUTECTIC MIXTURES CONTAINING ALKALI-METAL SULFONIMIDE SALTS, AND ELECTROCHEMICAL DEVICES UTILIZING SAME

RELATED APPLICATION DATA

This application claims the benefit of priority of U.S. Provisional Patent Application Ser. No. 62/779,772, filed Dec. 14, 2018, and titled "EUTECTIC MIXTURE FOR ELECTROCHEMICAL DEVICES", which is incorporated by reference herein in its entirety.

FIELD OF THE INVENTION

The present invention generally relates to the field of alkali-metal sulfonimide salts. In particular, the present invention is directed to eutectic mixtures containing alkali-metal sulfonimide salts, and electrochemical devices utilizing same.

BACKGROUND

Various kinds of electrolytes are used for electrochemical devices, such as secondary batteries, electrolytic condensers, electric double-layer capacitors, electrochromic display devices, and dye-sensitized solar cells, among others. Advances in such devices are increasing day by day, and the demands on and the requirements needed for the electrolytes of these advancing devices is likewise increasing.

Currently, the most electrolyte salts used are non-aqueous electrolytes, which are made by dissolving ionizable salts, such as lithium salt, in organic solvents, such as ethylene carbonate, propylene carbonate, dimethoxy ethane, and γ-butyrolactone. However, the use of organic solvents for such non-aqueous electrolytes often leads to leakage issues due to the resulting low viscosity and to vaporization due to their very strong volatility. These organic solvents are also flammable. Therefore, electrochemical devices utilizing electrolytes made using such organic solvents often experience problems with durability and stability.

To solve the flammability of liquid electrolytes in the context of lithium-ion secondary batteries, it has been proposed to use an imidazolium-based or ammonium-based ionic liquid as an electrolyte. However, such ionic liquids may be reduced at a higher voltage than lithium ions in the anode, or imidazolium or ammonium cations may be inserted into the anode together with lithium ions, which deteriorates the performance of the battery.

SUMMARY OF THE DISCLOSURE

In an implementation, the present disclosure is directed to an electrolyte, which includes a substantially eutectic mixture that includes a first salt, $X_1^+Y_1^-$, and a second salt, $X_2^+Y_2^-$, wherein each of $X1^+$ and $X_2^+$ is an alkali metal cation and $X1^+$ is different from $X_2^+$; and each of $Y_1^-$ and $Y_2^-$ is a sulfonimide anion and $Y_1^-$ is different from $Y_2^-$.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

DETAILED DESCRIPTION

Figure 1:
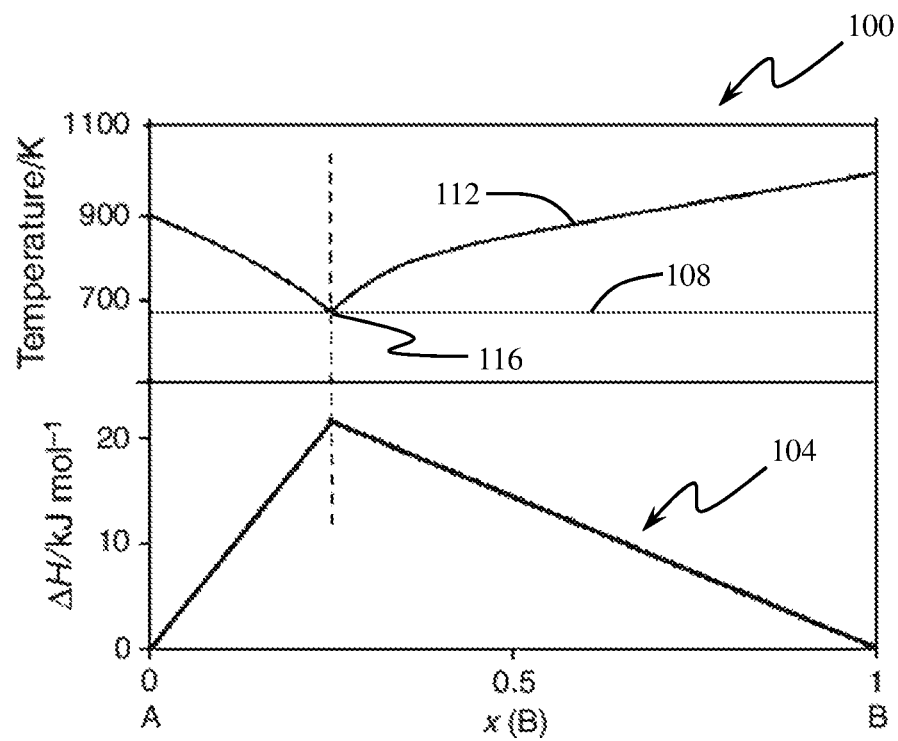
FIG. 1 is a combination of a eutectic phase diagram and a Tammann plot to illustrate an example method of determining the eutectic composition of a binary eutectic mixture of the present disclosure.

In some aspects, the present disclosure is directed to electrolytes comprising substantially eutectic mixtures containing two or more salts each composed of alkali-metal cations and corresponding sulfonimide anions. As used herein and in the appended claims, the term "substantially eutectic mixture" and like terms is used to indicate that the compositional ratios of the constituent salts are either at the theoretical eutectic point of the mixture or within an acceptable tolerance from the theoretical eutectic point, such as ±10%, ±5%, ±2%, or ±1%, depending on needs of a particular application of the particular electrolyte under consideration. In some embodiments, each of the eutectic mixtures of the present disclosure included in an electrolyte exhibits inherent characteristics of a eutectic mixture, such as wide electrochemical window, high conductance, excellent thermal stability, and excellent chemical stability, and also provides improvements to various problems, such as evaporation, ignition, and side reaction of an electrolyte caused by conventional usage of organic solvents.

In some embodiments, eutectic mixtures of the present disclosure have melting points equal to or less than about 73° C., less than about 65° C., or less than about 50° C. Consequently, in some embodiments eutectic mixtures of the present disclosure can function as molten salts in certain applications, such as for electrolytes for batteries and supercapacitors, among others. It is noted that throughout the present disclosure, the term "about" when used with a corresponding numeric value refers to ±20% of the numeric value, typically ±10% of the numeric value, often ±5% of the numeric value, and most often ±2% of the numeric value. In some embodiments, the term "about" can be taken as exactly indicating the actual numerical value.

In some embodiments, eutectic mixtures of the present disclosure and electrolytes made therewith can have viscosities in the range of about 1 centipoise (cP) to about 50 cP or in a range of about 5 cP to about 20 cP, among other ranges. In this connection, in some embodiments, it may be desirable to include at least one fluorinated additive, such as a fluorinated ether or a fluorinated glyme, to an electrolyte of the present disclosure, for example, to lower the viscosity and/or lower the melting temperature of the electrolyte. If included, the at least one fluorinated additive may be provided in an amount less than about 10% by weight of the electrolyte/eutectic mixture, such as in a range of about 1% to about 10% by weight.

In some embodiments, an electrolyte made in accordance with the present invention consists essentially of the alkali-metal sulfonimide salts in the eutectic mixture. Other matter, such as water, and/or protic or non protic solvent(s) may be unintentionally or unavoidably present, and such matter is specifically excluded under the term "consists essentially of" and like terms. In embodiments in which at least one fluorine-containing additive is present in an electrolyte of the present disclosure, the electrolyte may consist essentially of the alkali-metal sulfonimide salts in the eutectic mixture and the at least one fluorine-containing additive.

In another aspect, the present disclosure is directed to uses of electrolytes made in accordance with the present disclosure. For example, the electrolytes can be used in any suitable electrochemical device, such as a battery (secondary and primary) or supercapacitor, including a lithium-ion battery, a lithium-metal battery, lithium-sulfur battery, other alkali-metal-based battery, and sulfur-metal batteries, among others. As noted above, electrolytes made in accordance with the present disclosure can provide, for example, any one or more of wide electrochemical windows, high conductance, excellent thermal stability, and excellent chemical stability, and can also provide improvements to various problems, such as evaporation, ignition, and side reaction of an electrolyte caused by conventional usage of organic solvents, all of which can translate into more robust, higher-functioning electrochemical devices when compared to similar conventional electrochemical devices.

Details of the foregoing and other aspects of the present disclosure are described below.

Example Eutectic Mixtures

In some embodiments, eutectic mixtures containing two alkali-metal sulfonimide salts, i.e., binary eutectic mixtures, may be expressed as:

$$n(X_1^+Y_1^-)+m(X_2^+Y_2^-) \quad (1)$$

wherein:
$X_1^+Y_1^-$ is a first salt in which $X_1^+$ is an alkali-metal cation and $Y_1^-$ is a sulfonimide anion;
$X_2^+Y_2^-$ is a second salt in which $X_2^+$ is an alkali-metal cation and $Y_2^-$ is a sulfonimide anion;
n is the mole fraction of the first salt in the eutectic mixture;
m is the mole fraction of the second salt in the eutectic mixture; and n+m=1.

Being an alkali-metal ion, each of $X_1^+$ and $X_2^+$ is selected from the group consisting of $Li^+$, $Na^+$, $K^+$, $Rb^+$, $Cs^+$, and $Fr^+$, and in some embodiments, $X_1^+$ and $X_2^+$ are different from one another. Each of $Y_1^+$ and $Y_2^+$ may be, for example, $FSO_2N^-$ $SO_2F$ (FSI) or $FSO_2N^-$ $SO_2CF_3$ (FTFSI), and $Y_1^+$ and $Y_2^+$ are different from one another. A number of example binary eutectic mixtures appear in Table II, below. First, however, the following Table I shows molecular weights and melting points of individual alkali-metal sulfonimide salts that can be used to make various eutectic mixtures of the present disclosure.

TABLE I

PROPERTIES OF EXAMPLE
ALKALI-METAL SULFONIMIDE SALTS

| Salt | Symbol | Molecular Weight | Melting Point (° C.) |
|---|---|---|---|
| $FSO_2N(Li)SO_2F$ | LiFSI | 187 | 143 |
| $FSO_2N(K)SO_2F$ | KFSI | 219 | 102 |
| $FSO_2N(Rb)SO_2F$ | RbFSI | 265.4 | 96 |
| $FSO_2N(Cs)SO_2F$ | CsFSI | 313 | 115 |
| $FSO_2N(Li)SO_2CF_3$ | LiFTFSI | 237 | 101 |
| $FSO_2N(K)SO_2CF_3$ | KFTFSI | 269 | 102 |
| $FSO_2N(Rb)SO_2CF_3$ | RbFTFSI | 315.4 | 117 |
| $FSO_2N(Cs)SO_2CF_3$ | CsFTFSI | 363 | 107 |

In one example of finding the eutectic point to determine the values of the mole fractions n and m that define the eutectic mixture, a Tammann diagram can be constructed by formulating and testing several mixture compositions of the same salts but differing mole-fraction ratios. Referring to FIG. 1, this figure illustrates an example phase diagram 100 and an example Tammann diagram 104 for a binary system of compositions A and B. In the context of the present disclosure, A is either of the first and second fluorinated sulfonyl-imide salts, and B is the other of the fluorinated sulfonyl-imide salts. As those skilled in the art will understand, the phase diagram 100 shows a solidus temperature curve 108, a liquidus temperature curve 112, and a eutectic point 116.

As an initial step, differential scanning calorimetry (DSC) can be run on each of pure A and pure B independently. Then several, for example, three different mixture compositions, such as A:B molar ratios of 30:70, 50:50, and 30:70 are made and tested using DSC. Plotting the resulting melting temperature values can provide a rough idea of where the eutectic point will fall. The Tammann diagram 104 can be plotted to find the eutectic point 116 more precisely. Once the eutectic point 116, and correspondingly the values of n and m in Formula 1, above, have been determined from the Tammann diagram 104, the eutectic mixture can be made and tested using DSC to confirm that the actual melting temperature corresponds to the eutectic point 116 determined from the Tammann diagram 104. Table II, below, illustrates some example, but nonlimiting, binary eutectic mixtures of fluorinated sulfonyl-imide salts of the present disclosure as determined using this extrapolation and Tammann diagraming methodology.

TABLE II

EXAMPLE BINARY EUTECTIC MIXTURES

| Salt Mixture and Molar Composition | Eutectic Temp. (° C.) |
|---|---|
| LiFSI (0.39 mole) + KFTFSI (0.61 mole) | 65 |
| LiFSI (0.34 mole) + CsFTFSI (0.66 mole) | 43 |
| LiFSI (0.55 mole) + RbFTFSI (0.45 mole) | 47 |
| LiFTFSI (0.62 mole) + KFSI (0.38 mole) | 62 |
| LiFTFSI (0.65 mole) + CsFSI (0.35 mole) | 55 |
| LiFTFSI (0.64 mole) + RbFSI (0.36 mole) | 56 |
| LiFTFSI (0.64 mole) + KFTFSI (0.36 mole) | 63 |
| LiFTFSI (0.38 mole) + CsFTFSI (0.62 mole) | 53 |
| LiFTFSI (0.56 mole) + RbFTFSI (0.44 mole) | 70 |
| KFSI (0.52 mole) + CsFTFSI (0.48 mole) | 50 |
| KFSI (0.51 mole) + RbFTFSI (0.49 mole) | 63 |
| KFSI (0.48 mole) + KFTFSI (0.52 mole) | 73 |
| KFTFSI (0.37 mole) + CsFSI (0.63 mole) | 45 |
| KFTFSI (0.63 mole) + RbFSI (0.37 mole) | 49 |

In some embodiments, to make a binary eutectic mixture, the process may be carried out in a glovebox having the presence of water at <0.1 parts per million (ppm). In a typical experiment, a first fluorinated sulfonyl-imide salt in a mole fraction n and a second fluorinated sulfonyl-imide salt in a mole fraction m may be mixed properly by grinding, for example, using a mortar and pestle, to make a corresponding eutectic mixture. The melting point of the eutectic mixture may be measured using DSC. This is how the eutectic temperatures in Table II, above, were determined. Alternatively, a first fluorinated sulfonyl-imide salt in a mole fraction n and a second fluorinated sulfonyl-imide salt in a mole fraction m may be taken in a dry flask under and inert (e.g., Argon) atmosphere and dissolved in dimethyl carbonate to get a clear homogeneous solution. The solvent may be removed, e.g., at <0.01 Torr and at 35° C., to get a gel, which after a long evacuation time yields a eutectic mixture composition.

While the foregoing explanation and examples are directed to binary eutectic mixtures, the same principles can be extended to higher-order eutectic mixtures, such as ternary eutectic mixtures. In some embodiments, ternary eutectic mixtures of the present disclosure may be expressed as follows:

$$n(X_1^+Y_1^-)+m(X_2^+Y_2^-)+p(X_3^+Y_3^-) \quad (2)$$

wherein:
- $X_1^+Y_1^-$ is a first salt in which $X_1^+$ is an alkali-metal cation and $Y_1^-$ is a sulfonimide anion;
- $X_2^+Y_2^-$ is a second salt in which $X_2^+$ is an alkali-metal cation and $Y_2^-$ is a sulfonimide anion;
- $X_3^+Y_3^-$ is a third salt in which $X_3^+$ is an alkali-metal cation and $Y_3^-$ is a sulfonimide anion;
- n is the mole fraction of the first salt in the eutectic mixture;
- m is the mole fraction of the second salt in the eutectic mixture;
- p is the mole fraction of the third salt in the eutectic mixture; and
- n+m+p=1.

Being an alkali-metal ion, each of $X_1^+$, $X_2^+$, and $X_3^+$ is selected from the group consisting of $Li^+$, $Na^+$, $K^+$, $Rb^+$, $Cs^+$, and $Fr^+$, and in some embodiments, at least two of $X_1^+$, $X_2^+$ and $X_3^+$ are different from one another. Each of $Y_1^+$, $Y_2^+$, and $Y_3^+$ may be, for example, FSI or FTFSI. In some embodiments, at least two of $Y_1^+$, $Y_2^+$, and $Y_3^+$ are different from one another, while in some embodiments all of $Y_1^+$, $Y_2^+$, and $Y_3^+$ are the same as one another.

In some embodiments, to make ternary eutectic mixture, in a typical experiment, a first fluorinated sulfonyl-imide salt in a mole fraction n may be taken in a dry flask in a glovebox (see above) and mixed with a second fluorinated sulfonyl-imide salt in a mole fraction m followed by the addition of a third fluorinated sulfonyl-imide salt in a mole fraction p. The resulting ternary eutectic mixture may be heated until a liquid eutectic mixture is obtained. To make the mixture homogeneous, it may be well mixed using a stirring bar. The obtained ternary eutectic mixture melting point may be determined by using DSC. The electrochemical window may also be measured to determine the electrochemical redox stability.

A eutectic is a composition of a minimum of two or more components, each of which melts and freezes congruently. During the crystallization phase, a mixture of the components is formed that acts as a single composition. The components freeze to an intimate mixture of crystals and melt simultaneously without separation. Eutectics can be mixtures of organic and/or inorganic compounds. Hence, eutectics can be made as either organic-organic, inorganic-inorganic, or organic-inorganic mixtures. This gives room for a wide variety of combinations that can be tailored for specific applications. Benefits of eutectic mixtures include their ability to obtain more desired properties, such as a specific melting point or a higher heat storage capacity per unit volume.

Example Electrolytes Using Eutectic Mixtures (Molten Salts)

Eutectic mixtures of the present disclosure, such as the eutectic mixtures described above and exemplified below, can be used as molten-salt electrolytes for any suitable purpose, such as providing an electrolyte for an electrochemical device, including any of the electrochemical devices mentioned above. In some embodiments, molten-salt electrolytes of the present disclosure have melting points in the range of about 5° C. to about 70° C. In some embodiments, molten-salt electrolytes of the present disclosure have melting points in the range of about 5° C. to about 30° C. In some embodiments, molten-salt electrolytes of the present disclosure have melting points in the range of about 30° C. to about 50° C. In some embodiments, molten-salt electrolytes of the present disclosure have melting points in the range of about 50° C. to about 70° C. In some embodiments, each molten-salt electrolyte may consist essentially of the eutectic mixture, i.e., not have any additive intentionally added to provide some desired effect. In some embodiments, at least one additive may be provided to the molten-salt electrolyte with one or more benefits. For example, at least one fluorine-containing additive, such as a mono fluorine containing additive, such as fluoroethylene carbonate (FEC), a di fluorine containing additive, such as difluoroethylene carbonate (DEC), a tri fluorine containing additive such as $CF_3SO_2NH_2$, fluorinated triethylphosphine oxide, fluorinated carbonates, such as trifluoromethylethyl methyl carbonate, $CF_3CH_2CO_3CH_3$ or a fluorinated ether, or any combination thereof, among others, can be used to decrease the viscosity of the molten-salt electrolyte and/or reduce the melting temperature of the molten-salt electrolyte. In some embodiments, the at least one fluorine-containing additive is provided to the molten-salt electrolyte in an amount less than about 10%, by weight, relative to the molten-salt electrolyte. For example, in such embodiments, the at least one fluorine-containing additive is provided to the molten-salt electrolyte in an amount ranging from about 1% to about 10%, by weight. In some embodiments, each molten-salt electrolyte containing at least additives, such as at least one fluorine-containing additive, may consist essentially of the eutectic mixture (binary, ternary, etc.) and the at least one additive.

EXPERIMENTAL RESULTS

The above methodologies are further illustrated by the following examples, although it will be understood that these examples are included merely for purposes of illustration and are not intended to limit the scope of the present disclosure. The examples presented herein are just for better understandings of aspects of the scope of the disclosure to persons having ordinary skill in the art. Unless otherwise stated, all chemicals used in the described examples were of high purity (>99%). Stringent precautions were taken to exclude the moisture in the process and reactions were performed in well ventilated hoods.

Example 1

Synthesis of LiFSI and CsFTFSI binary eutectic mixture: This operation was carried out in a glovebox having a water of <0.1 ppm. LiFSI (0.34 mole) and CsFTFSI (0.66 mole) were mixed properly by grinding with a mortar and pestle. The eutectic mixture melting point was measured using DSC. The eutectic mixture melting point was found to be 43° C.

Example 2

Synthesis of LiFSI and RbFTFSI binary eutectic mixture: This operation was carried out in a glovebox having a water of <0.1 ppm. LiFSI (0.55 mole) and RbFTFSI (0.45 mole) were mixed properly by grinding with a mortar and pestle. The eutectic mixture melting point was measured using DSC. The eutectic mixture melting point was found to be 47° C.

Example 3

Synthesis of LiFTFSI and KFSI binary eutectic mixture: This operation was carried out in a glovebox having a water of <0.1 ppm. LiFTFSI (0.62 mole) and KFSI (0.38 mole) were mixed properly by grinding with a mortar and pestle. The eutectic mixture melting point was measured using DSC. The eutectic mixture melting point was found to be 62° C.

Example 4

Synthesis of LiFTFSI and CsFSI binary eutectic mixture: This operation was carried out in a glovebox having a water of <0.1 ppm. LiFTFSI (0.65 mole) and CsFSI (0.35 mole) were mixed properly by grinding with a mortar and pestle. Eutectic mixture melting point was measured using DSC. Eutectic mixture melting point was found to be 55° C.

Example 5

Synthesis of LiFTFSI and RbFSI binary eutectic mixture: This operation was carried out in a glovebox having a water of <0.1 ppm. LiFTFSI (0.64 mole) and RbFSI (0.36 mole) were mixed properly by grinding with a mortar and pestle. The eutectic mixture melting point was measured using DSC. The eutectic mixture melting point was found to be 56° C.

Example 6

Synthesis of LiFTFSI and CsFTFSI binary eutectic mixture: This operation was carried out in a glovebox having a water of <0.1 ppm. LiFTFSI (0.38 mole) and CsFTFSI (0.62 mole) were mixed properly by grinding with a mortar and pestle. Eutectic mixture melting point was measured using DSC. Eutectic mixture melting point was found to be 53° C.

Example 7

Synthesis of KFSI and CsFTFSI binary eutectic mixture: This operation was carried out in a glovebox having a water of <0.1 ppm. KFSI (0.52 mole) and CsFTFSI (0.48 mole) were mixed properly by grinding with a mortar and pestle. The eutectic mixture melting point was measured using DSC. The eutectic mixture melting point was found to be 50° C.

Example 8

Synthesis of KFTFSI and CsFSI binary eutectic mixture: This operation was carried out in a glovebox having a water of <0.1 ppm. KFTFSI (0.37 mole) and CsFSI (0.63 mole) were mixed properly by grinding with a mortar and pestle. The eutectic mixture melting point was measured using DSC. The eutectic mixture melting point was found to be 45° C.

Example 9

Synthesis of KFTFSI and RbFSI binary eutectic mixture: This operation was carried out in a glovebox having a water of <0.1 ppm. KFTFSI (0.63 mole) and RbFSI (0.37 mole) were mixed properly by grinding with a mortar and pestle. The eutectic mixture melting point was measured using DSC. The eutectic mixture melting point was found to be 49° C.

Example 10

Synthesis of LiTFSI, KFTFSI and CsFTSI ternary eutectic mixture: This operation was carried out in a glovebox having a water of <0.1 ppm. LiFTFSI (0.35 mole), KFTFSI (0.30 mole) and CsFTFSI (0.35 mole) were mixed properly by grinding with a mortar and pestle. The eutectic mixture melting point was measured using DSC. The eutectic mixture melting point was found to be <70° C.

Example 11

Synthesis of LiFTFSI, RbFSI and CsFTFSI ternary eutectic mixture: This operation was carried out in a glovebox having a water of <0.1 ppm. LiFTFSI (0.35 mole), RbFSI (0.35 mole), and CsFTFSI (0.30 mole) were mixed properly by grinding with a mortar and pestle. The eutectic mixture melting point was measured using DSC. The eutectic mixture melting point was found to be <70° C.

Example 12

Synthesis of LiFTFSI, KFSI and CsFTFSI ternary eutectic mixture: This operation was carried out in a glovebox having a water of <0.1 ppm. LiFTFSI (0.36 mole), KFSI (0.34 mole), and CsFTFSI (0.30 mole) were mixed properly by grinding with a mortar and pestle. The eutectic mixture melting point was measured using DSC. The eutectic mixture melting point was found to be <70° C.

Example Uses of Molten-Salt Electrolytes of the Present Disclosure

Figure 2:
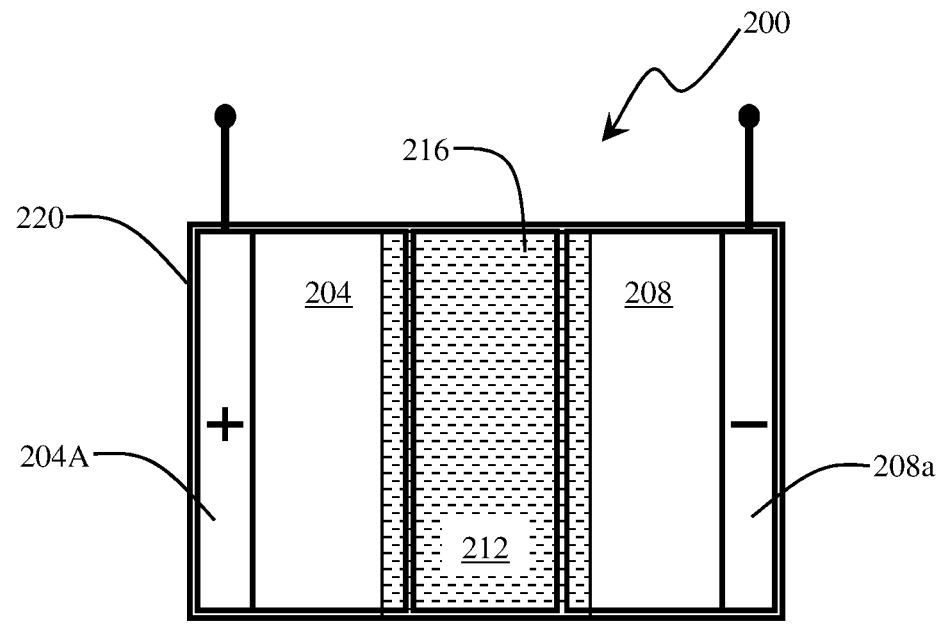
FIG. 2 is a high-level diagram illustrating an electrochemical device made in accordance with aspects of the present disclosure.

As mentioned above, a molten-salt electrolyte of the present disclosure may be used as an electrolyte for an electrochemical device, among other things. FIG. 2 illustrates an electrochemical device 200 made in accordance with aspects of the present disclosure. Those skilled in the art will readily appreciate that the electrochemical device 200 can be, for example, a battery or a supercapacitor. In addition, those skilled in the art will readily understand that FIG. 2 illustrates only some basic functional components of the electrochemical device 200 and that a real-world instantiation of the electrochemical device, such as a secondary battery or a supercapacitor, will typically be embodied using either a wound construction or a stacked construction. Further, those skilled in the art will understand that the electrochemical device 200 will include other components, such as electrical terminals, seal(s), thermal shutdown layer(s), and/or vent(s), among other things, that, for ease of illustration, are not shown in FIG. 2.

In this example, the electrochemical device 200 includes spaced-apart positive and negative electrodes 204, 208, respectively, and a pair of corresponding respective current collectors 204A, 208A. A porous dielectric separator 212 is located between the positive and negative electrodes 204, 208 to electrically separate the positive and negative electrodes but to allow ions of a molten-salt electrolyte 216 made in accordance with the present disclosure to flow therethrough. The porous dielectric separator 212 and/or one, the other, or both of the positive and negative electrodes 204, 208, if porous, is/are impregnated with the molten-salt electrolyte 216. In FIG. 2, both the positive and negative electrodes 204, 208 are illustrated as being porous by way of the molten-salt electrolyte 216 being illustrated as extending into them. As described above, benefits of using a molten-salt electrolyte of the present disclosure for molten-salt electrolyte 216 can include providing wide electrochemical windows, high conductance, excellent thermal stability, and excellent chemical stability, and can also provide improvements to various problems, such as evaporation, ignition, and side reaction of an electrolyte caused by conventional usage of organic solvents, all of which can translate into more robust, higher-functioning electrochemical devices when compared to similar conventional electrochemical devices. Examples of molten-salt electrolytes suitable for use as the molten-salt electrolyte 216 are described above. The electrochemical device 200 includes a container 220 that contains the current collectors 204A, 208A, the positive and negative electrodes 204, 208, the porous dielectric separator 212, and the molten-salt electrolyte 216.

As those skilled in the art will understand, depending upon the type and design of the electrochemical device, each of the positive and negative electrodes 204, 208 comprises a suitable material compatible with the alkali-metal ions and other constituents in the molten-salt electrolyte 216. Each of the current collectors 204A, 208A may be made of any suitable electrically conducting material, such as copper or aluminum, or any combination thereof. The porous dielectric separator 212 may be made of any suitable porous dielectric material, such as a porous polymer, among others. Various battery and supercapacitor constructions that can be used for constructing the electrochemical device 200 of FIG. 2, are known in the art. If any of such known constructions is used, a novelty of electrochemical device 200 lies in the composition of the molten-salt electrolyte 216.

In some examples, aspects of the present disclosure may also include an electrochemical device. The device includes a positive electrode; a negative electrode spaced from the positive electrode; a porous dielectric separator located between the positive and negative electrodes; and any of the electrolytes as recited in any of original claims 1-30 of the present application, as filed, the electrolytes contained within at least the porous dielectric separator.

The foregoing has been a detailed description of illustrative embodiments of the invention. It is noted that in the present specification and claims appended hereto, conjunctive language such as is used in the phrases "at least one of X, Y and Z" and "one or more of X, Y, and Z," unless specifically stated or indicated otherwise, shall be taken to mean that each item in the conjunctive list can be present in any number exclusive of every other item in the list or in any number in combination with any or all other item(s) in the conjunctive list, each of which may also be present in any number. Applying this general rule, the conjunctive phrases in the foregoing examples in which the conjunctive list consists of X, Y, and Z shall each encompass: one or more of X; one or more of Y; one or more of Z; one or more of X and one or more of Y; one or more of X and one or more of Z; one or more of Y and one or more of Z; and one or more of X, one or more of Y and one or more of Z.

Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve aspects of the present disclosure. Accordingly, this description is meant to be taken only by way of example, and not to otherwise limit the scope of this invention.

What is claimed is:

1. An electrolyte, comprising:
a substantially eutectic mixture that includes a first salt, $X_1^+Y_1^-$, and a second salt, $X_2^+Y_2^-$, wherein:
each of $X_1^+$ and $X_2^+$ is an alkali metal cation and $X_1^+$ is different from $X_2^+$;
each of $Y_1^-$ and $Y_2^-$ is a sulfonimide anion and $Y_1^-$ is different from $Y_2^-$; and
the electrolyte has an electrical window from 0V to about 5V.

2. The electrolyte of claim 1, wherein the substantially eutectic mixture has a melting temperature and a viscosity, and the electrolyte further comprises a fluorine-containing additive that lowers the melting temperature and lowers the viscosity.

3. The electrolyte of claim 2, wherein the fluorine-containing additive forms from about 1% to about 10% of the electrolyte, by weight.

4. The electrolyte of claim 2, wherein the electrolyte consists essentially of the first salt, the second salt, and the fluorine-containing additive.

5. The electrolyte of claim 2, wherein the viscosity is in a range of about 1 cP to about 50 cP.

6. The electrolyte of claim 5, wherein the viscosity is in a range of about 5 cP to about 20 cP.

7. The electrolyte of claim 1, wherein the electrolyte consists essentially of the first salt and the second salt.

8. The electrolyte of claim 1, wherein the substantially eutectic mixture has a melting temperature of about 73° C. or less.

9. The electrolyte of claim 8, wherein the melting temperature is about 65° C. or less.

10. The electrolyte of claim 9, wherein the melting temperature is about 50° C. or less.

11. The electrolyte of claim 1, wherein $Y_1^-$ and $Y_2^-$ are selected from the group consisting of $FSO_2N^- SO_2F$ (FSI$^-$) and $FSO_2N^- SO_2CF_3$ (FTFSI$^-$).

12. The electrolyte of claim 11, wherein $X_1^+$ and $X_2^+$ are selected from the group consisting of Li$^+$, Na$^+$, K$^+$, Rb$^+$, and Cs$^+$.

13. The electrolyte of claim 1, wherein the substantially eutectic mixture has a melting temperature in a range of about 5° C. to about 70° C.

14. The electrolyte of claim 1, wherein the substantially eutectic mixture has a melting temperature in a range of about 30° C. to about 70° C.

15. The electrolyte of claim 1, wherein the substantially eutectic mixture has a melting temperature in a range of about 5° C. to about 30° C.

16. The electrolyte of claim 1, further comprising a third salt, $X_3^+Y_3^-$, wherein $X_3^+$ is an alkali-metal cation that is different from each of $X_1^+$ and $X_2^+$, and $Y_3^-$ is a sulfonimide anion.

17. The electrolyte of claim 16, wherein the substantially eutectic mixture has a melting temperature and a viscosity, and the electrolyte further comprises a fluorine-containing additive that lowers the melting temperature and lowers the viscosity.

18. The electrolyte of claim 17, wherein the fluorine-containing additive forms from about 1% to about 10% of the electrolyte, by weight.

19. The electrolyte of claim 17, wherein the electrolyte consists essentially of the first salt, the second salt, the third salt, and the fluorine-containing additive.

20. The electrolyte of claim 17, wherein the viscosity is in a range of about 1 cP to about 50 cP.

21. The electrolyte of claim 20, wherein the viscosity is in a range of about 5 cP to about 20 cP.

22. The electrolyte of claim 16, wherein the electrolyte consists essentially of the first salt, the second salt, and the third salt.

23. The electrolyte of claim 16, wherein the substantially eutectic mixture has a melting temperature of about 73° C. or less.

24. The electrolyte of claim 23, wherein the melting temperature is about 65° C. or less.

25. The electrolyte of claim 24, wherein the melting temperature is about 50° C. or less.

26. The electrolyte of claim 16, wherein $Y_1^-$, $Y_2^-$, and $Y_3^-$ are selected from the group consisting of $FSO_2N^- SO_2F$ (FSI$^-$) and $FSO_2N^- SO_2CF_3$ (FTFSI$^-$).

27. The electrolyte of claim 26, wherein $X_1^+$, $X_2^+$, and $X_3^+$ are selected from the group consisting of Li$^+$, Na$^+$, K$^+$, Rb$^+$, and Cs$^+$.

28. The electrolyte of claim 16, wherein the substantially eutectic mixture has a melting temperature in a range of about 5° C. to about 70° C.

29. An electrolyte, comprising:
a substantially eutectic mixture that includes a first salt, $X_{1+}Y_{1-}$, and a second salt, $X_{2+}Y_{2-}$, wherein:
each of $X_{1+}$ and $X_{2+}$ is an alkali metal cation and $X_{1+}$ is different from $X_{2+}$;
each of $Y_{1-}$ and $Y_{2-}$ is a sulfonimide anion and $Y_{1-}$ is different from $Y_{2-}$;
the substantially eutectic mixture has a melting temperature and a viscosity, and the electrolyte further comprises a fluorine-containing additive that lowers the melting temperature and lowers the viscosity; and
the viscosity is in a range of about 1 cP to about 50 cP.

30. An electrolyte, comprising:
a substantially eutectic mixture that includes a first salt, $X_{1+}Y_{1-}$, and a second salt, $X_{2+}Y_{2-}$, wherein:
each of $X_{1+}$ and $X_{2+}$ is an alkali metal cation and $X_{1+}$ is different from $X_{2+}$;
each of $Y_{1-}$ and $Y_{2-}$ is a sulfonimide anion and $Y_{1-}$ is different from $Y_{2-}$; and
the substantially eutectic mixture has a melting temperature in a range of about 5° C. to about 30° C.

\* \* \* \* \*